(12) United States Patent
Smith et al.

(10) Patent No.: US 7,314,373 B1
(45) Date of Patent: Jan. 1, 2008

(54) APPARATUS FOR PULLING LOOSE TEETH

(76) Inventors: Roderick L. Smith, 2611 Withington Peak Dr., Rio Rancho, NM (US) 87144; Ryan L. Smith, 9519 Parkwood Dr., Grand-Blanc, MI (US) 48439

( * ) Notice: Subject to any disclaimer, the term of this patent is extended or adjusted under 35 U.S.C. 154(b) by 61 days.

(21) Appl. No.: 11/270,107

(22) Filed: Nov. 9, 2005

(51) Int. Cl.
*A61C 3/14* (2006.01)
(52) U.S. Cl. ..................................... 433/159
(58) Field of Classification Search ......... 433/159–160
See application file for complete search history.

(56) References Cited

U.S. PATENT DOCUMENTS

| 740,549 | A | | 10/1903 | Gilbert |
| 1,033,942 | A | | 7/1912 | Ruggles |
| 2,696,048 | A | | 12/1954 | Lindgren |
| 4,001,940 | A | | 1/1977 | Cusato |
| 4,245,859 | A | * | 1/1981 | Rainin .......................... 294/1.2 |
| 6,045,360 | A | * | 4/2000 | Simoes ........................ 433/141 |
| 6,322,363 | B1 | | 11/2001 | Beecher et al. |
| 6,431,864 | B1 | * | 8/2002 | Silverstein .................. 433/159 |

\* cited by examiner

*Primary Examiner*—Kimberly S. Smith
*Assistant Examiner*—Heidi Bashaw
(74) *Attorney, Agent, or Firm*—Young Basile

(57) ABSTRACT

An apparatus for pulling loose teeth having a releasably attachable decorative element for soothing the patient. The apparatus of the present invention provides a first arm and a second arm each with a decorative end and a tool end wherein the first and second arms are connected at the decorative ends. The tool ends of the first and second arms are moveable between a first position, wherein the tool ends of the first and second arms are adapted to disengage the tooth, and a second position, wherein the tool ends of the first and second arms are adapted to engage the tooth. A decorative element is releasably attachable to the decorative end of the first and second arms.

11 Claims, 2 Drawing Sheets

APPARATUS FOR PULLING LOOSE TEETH

FIELD OF THE INVENTION

The present invention relates to dental tools, and more particularly, the present invention relates to an apparatus for pulling a loose tooth from the mouth of a child.

BACKGROUND OF THE INVENTION

Children typically lose their baby teeth prior to adolescence. Due to the anxiety created from pain and blood, children may avoid further loosening and removing their baby teeth from their mouths. Various methods have been utilized to quickly and painlessly remove children's teeth. For instance, people have used string to surround the tooth and pull it from the mouth. Other people have used various forms of food and other materials that loosen teeth when they are bitten into to aid in removal of the tooth from the child's mouth. The visual and tactile sensations produced by these methods create anxiety and tension in young children due to their peculiar association with the pain of tooth removal.

It would be desirable to have an apparatus for pulling loose teeth from a child's mouth without creating anxiety and tension.

SUMMARY OF THE INVENTION

The present invention relates to an apparatus for pulling loose teeth having a releasably attachable decorative element for soothing the patient. The apparatus for pulling loose teeth includes a first arm and a second arm that each have a decorative end and a tool end. The first and second arms are connected to one another at the decorative ends. The decorative element may be attached to the first and second arms through engagement of an attachment member on the decorative element with a receptacle, such as an aperture, on the decorative ends of the first and second arms.

To reduce the magnitude of unpleasant sensations experienced by the patient and to enhance the grip on the tooth, engagement tips may be provided upon each of the first and second arms. The engagement tips may be made of a resilient material, such as rubber. Furthermore, the engagement tips may be fabricated from rubber caps.

The first and second arms may move between a first position, wherein the tool ends of the first and second arms are adapted to disengage the tooth, and a second position, wherein the tool ends of the first and second arms are adapted to engage the tooth. The first and second arms may be biased toward the first position. Furthermore, the first and second arms may be integrally formed.

To maintain the decorative element within the view of the patient, the engagement tips may be located at the ends of upturned portions that extend at obtuse angles from the arms. Furthermore, the decorative element may be attached adjacent to either a top or bottom surface of the decorative ends of the first and second arms so that the decorative element remains visible regardless of whether the tooth being pulled is in the patient's upper jaw or lower jaw.

BRIEF DESCRIPTION OF THE DRAWINGS

The description herein makes reference to the accompanying drawings wherein like referenced numerals refer to like parts throughout several views and wherein.

DETAILED DESCRIPTION OF THE INVENTION

Figure 1:
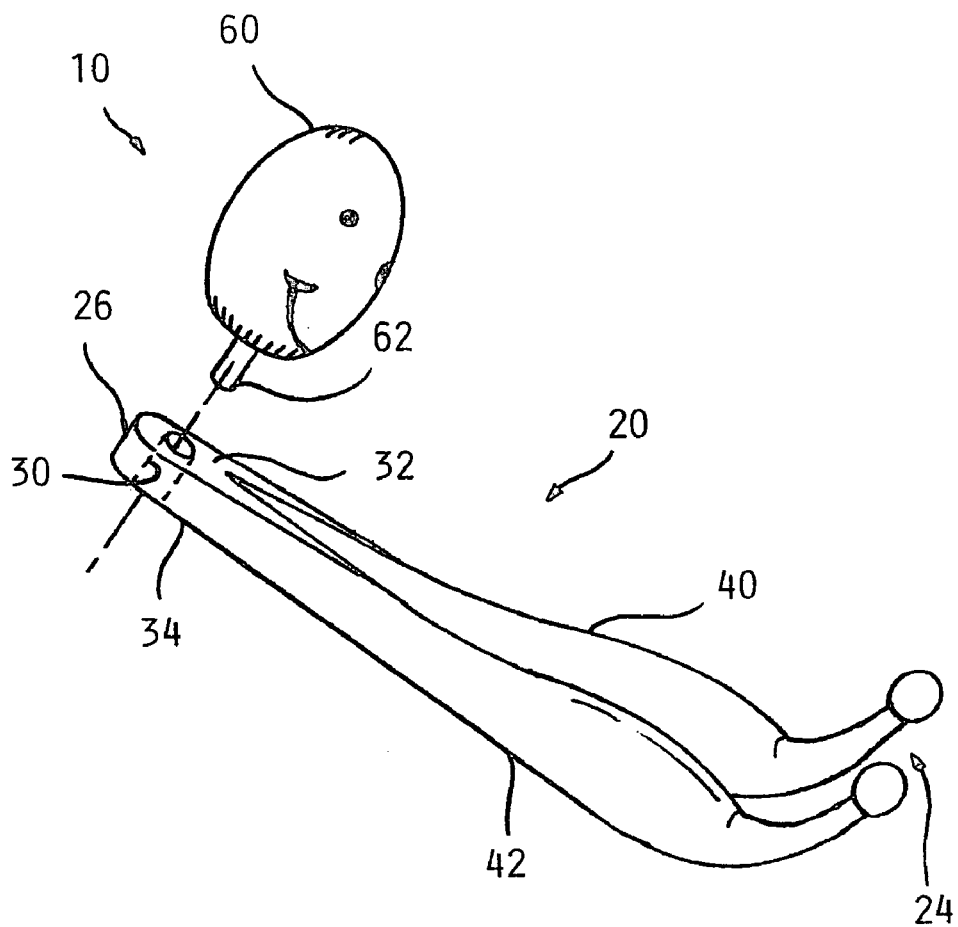
FIG. 1 is a perspective view of the apparatus for pulling teeth of the present invention.

Referring to the drawings, the present invention will now be described in detail with reference to the disclosed embodiment.

FIG. 1 shows an apparatus 10 of the present invention for pulling a loose tooth (not shown) from the mouth of a patient (not shown). The apparatus 10 includes a handle portion 20 having a pair of arms, such as a first arm 40 and a second arm 42, wherein the first and second arms 40, 42 each have a tool end 24 and a decorative end 26. The first and second arms 40, 42 are connected to one another at the decorative end 26 and are not connected at the tool end 24. The first and second arms 40, 42 may move between a first position, wherein the tool ends 24 of the first and second arms 40, 42 are spaced apart so as not to engage an object, such as the tooth, and a second position, wherein the tool ends 24 of the arms 40, 42 are adjacent one another to engage opposite sides of a gripped object, such as the tooth. The apparatus 10 further includes a decorative element 60 that is releasably attachable to the decorative ends 26 of the first and second arms 40, 42.

Figure 2:
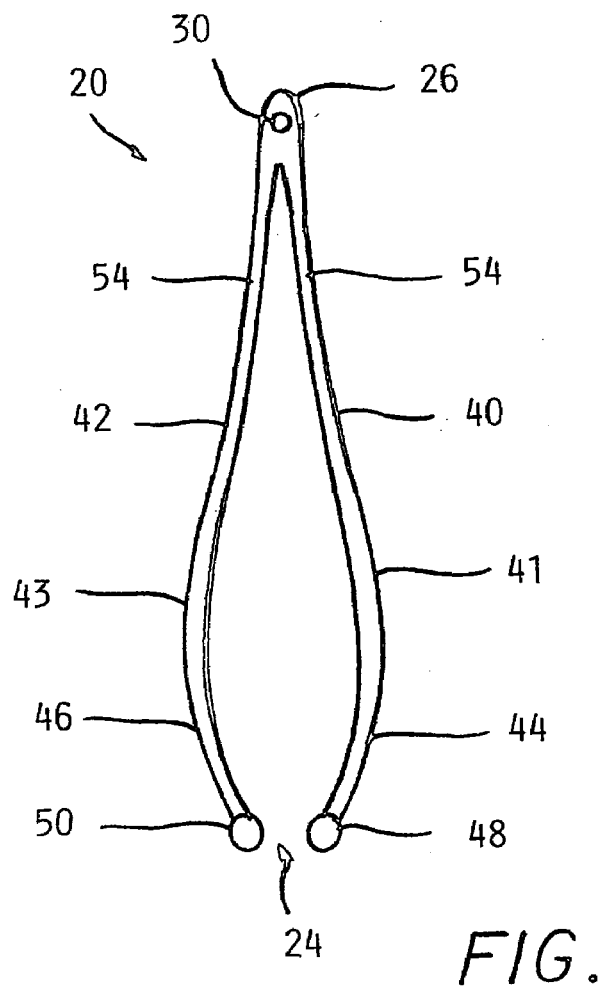
FIG. 2 is a top view of the handle portion of the apparatus for pulling teeth of the present invention.
Figure 3:
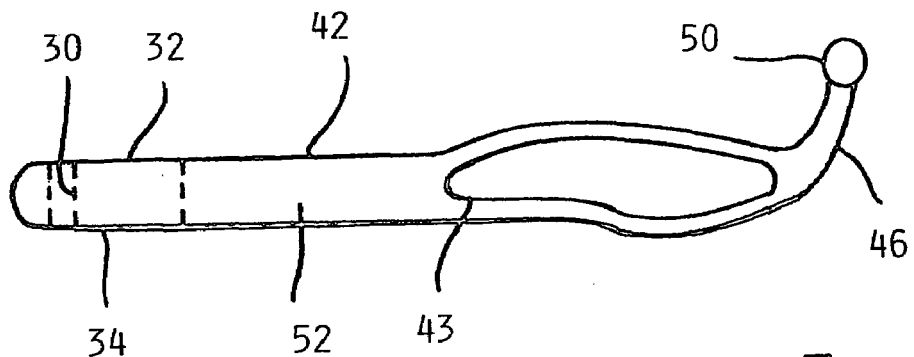
FIG. 3 is a side view of the handle portion of the apparatus for pulling teeth of the present invention.

As shown in FIGS. 2-3, the first and second arms 40, 42 of the handle portion 20 are elongated bodies that are connected at the decorative ends 26 of the first and second arms 40, 42 and not connected at the tool ends 24 of the first and second arms 40, 42. The first and second arms 40, 42 are connected by a fixed, integral connection between the decorative ends 26 of the arms 40, 42, wherein the arms 40, 42 are formed from a resilient material, such as metallic or polypropylene material, such that the arms 40, 42 may flex with respect to one another, thereby allowing the tool ends 24 of the first and second arms 40, 42 to move between the first and second positions. In this regard, the arms 40, 42 may be formed as portions of an integral handle portion 20 that meet at the decorative ends 26. Alternatively, the connection between the first and second arms 40, 42 at the decorative ends 26 of the first and second arms 40, 42 may be formed by a hinge, a spring, a piston, a bolt, a weld, a soldered connection, an adhesive bond, or any other suitable structure. Furthermore, the decorative ends 26 of the first and second arms 40, 42 may include a top surface 32 and a bottom surface 34 defined at the connection between the first and second arms 40, 42. A receptacle 30 may be connected to the decorative ends 26 of the first and second arms 40, 42. The receptacle 30 allows for releasable attachment of the decorative element 60 (shown in FIG. 1) to the handle portion 20 and will be described in detail herein.

Each of the first and second arms 40, 42 of the handle portion 20 has an elongated body extending from the decorative end 26 to the tool end 24. Each elongated body has a substantially flat, broad side surface 52 and a narrow top surface 54. Although the first and second arms 40, 42 are generally uniform in height, the side surfaces 52 of the arms 40, 42 may increase in height at a first widened portion 41 and second widened portion 43 on the first and second arms 40, 42, respectively. The first and second widened portions 41, 43 allow a user a greater surface area for gripping and may be provided with a surface that increases the friction between the first and second widened portions 41, 43 and the user's hand, such as serrations, textures, rubberized pads, or other similar structures.

Adjacent to the first and second widened portions 41, 43 and further toward the tool ends 24 of the first and second arms 40, 42, a first upturned portion 44 and a second upturned portion 46 extend from each of the first and second arms 40, 42, respectively. At the first and second upturned portions 44, 46, the side surfaces 52 of the first and second arms 40, 42 substantially decrease in height as they extend toward the tool end 24. The first and second upturned portions 44, 46 form an obtuse angle with respect to the remainder of the first and second arms 40, 42. At the tool end 24, each of the first and second upturned portions 44, 46 terminates at a tooth engaging element, such as a first engagement tip 48 and a second engagement tip 50 of the first and second arms 40, 42. The first and second engagement tips 48, 50 may function to engage and grip an object, such as the loose tooth. The first and second engagement tips 48, 50 may be formed from a resilient material, such as rubber. Furthermore, the first and second engagement tips 48, 50 may also be fabricated from rubber caps.

In order to engage and disengage the tooth, the first position of the first and second arms 40, 42 of the handle portion 20 may be defined by the first and second engagement tips 48, 50 being spaced apart such that the first and second arms 40, 42 are disengaged from opposite sides of the tooth. The second position of the first and second arms 40, 42 may be defined by the first and second engagement tips 48, 50 being engaged with opposite sides of a gripped object, such as the tooth.

In the first position, the first and second arms 40, 42 of the handle portion 20 are biased away from one another. The biasing force may be provided by the resilient nature of the material that the first and second arms 40, 42 are constructed from, such that the first and second arms 40, 42 return to the first position when in their relaxed position. Alternatively, the biasing force upon the first and second arms 40, 42 may be provided by any conventional biasing element including, but not limited to, a spring.

The first and second arms 40, 42 of the handle portion 20 are moveable from the first position to the second position in response to a force applied at an intermediate point along the first and second arms 40, 42. For example, such a force may be applied to the side surfaces 52 of the first and second arms 40, 42 at the first and second widened portions 41, 43 by the user's fingers (not shown). Accordingly, the first and second arms 40, 42 may act as a pair of third-class levers. Generally, a third-class lever has a fulcrum at a first end, and applies a force at a second end in response to a force applied to the lever at an intermediate point. In this case, the connected decorative ends 26 of the first and second arms 40, 42 may act as a fulcrum for both the first and second arms 40, 42 to thereby allow a force to be applied by the engagement tips 48, 50 in response to a force applied to the first and second arms 40, 42 at the first and second widened portions 41, 43.

Referring again to FIG. 1, the decorative element 60 of the apparatus 10 serves to amuse the patient by relaxing the patient while the apparatus 10 is being used to remove the tooth from the patient's mouth. The decorative element 60 may be formed in many amusing configurations or shapes, such as characters, figures, plants, or animals. Furthermore, the decorative element 60 may be formed from one of many materials including, but not limited to, plastics, metals, or textiles. Additionally, the decorative element 60 may include a noisemaker, such as a horn or bell, or the decorative element 60 may include one or several lights.

The decorative element 60 is releasably attachable to the handle portion 20 of the apparatus 10 by means of an attachment member 62 located on the decorative element 60. The attachment member 62 cooperatively engages the receptacle 30 to allow for selective attachment and detachment of the decorative element 60 to the handle portion 20. The attachment member 62 may be a post, and the receptacle 30 may be an aperture formed in the decorative ends 26 such that the attachment member 62 is received by the receptacle 30 to form a friction fit. The aperture of the receptacle 30 extends through the decorative ends 26 between the top surface 32 and the bottom surface 34, thereby allowing the attachment member 62 to be received in the receptacle 30 such that the decorative element 60 is located adjacent to either the top surface 32 or the bottom surface 34 of the decorative ends 26. Alternatively, the attachment member 62 and the receptacle 30 may be selected from any known attachment means operative to provide secure releasable attachment of the decorative element 60 to the handle portion 20. For example, the attachment member 62 may be a clip, and the receptacle 30 may be a cooperative post, ring, or the like. As another example, the attachment member 62 and the receptacle 30 may be cooperatively threaded elements. Furthermore, multiple receptacles 30 may be provided upon the decorative ends 26 of the first and second arms 40, 42 to thereby allow the decorative element 60 to be selectively attached to the handle portion 20 in one of two or more positions with respect to the decorative ends 26 of the first and second arms 40, 42.

In use, the apparatus 10 for pulling loose teeth of the present invention is utilized to remove a tooth from a patient's mouth. The user first selects an appropriate decorative element 60. A broad variety of decorative elements 60 may be provided such that the decorative element 60 may be selected with consideration to the age, gender, and particular tastes of the patient.

After the decorative element 60 is selected, the user attaches the decorative element 60 to the handle portion 20 of the apparatus 10. As previously described, embodiments of the apparatus 10 are contemplated wherein the receptacle 30 allows the decorative element 60 to be attached adjacent to the top surface 32 or the bottom surface 34 of the decorative ends 26 of the first and second arms 40, 42, thereby allowing the decorative element 60 to be placed in the line of sight of the patient. Particularly, since the upturned portions 44, 46 are intended to extend toward the loose tooth while the loose tooth is being pulled, the top surface 32 of the decorative ends 26 faces the patient if the loose tooth resides in the patient's upper jaw, and the bottom surface 34 of the decorative ends 26 faces the patient if the loose tooth is in the patient's lower jaw. Accordingly, if the tooth to be pulled is in the patient's upper jaw, the user connects the attachment member 62 of the decorative element 60 to the receptacle 30 on the handle portion 20 such that the decorative element 60 is located adjacent the top surface 32 of the decorative ends 26 of the first and second arms 40, 42. If the tooth to be pulled is in the patient's lower jaw, the user connects the attachment member 62 of the decorative element 60 to the receptacle 30 on the handle portion 20 such that the decorative element 60 is located adjacent the bottom surface 34 of the decorative ends 26 of the first and second arms 40, 42.

After the decorative element 60 is secured to the handle portion 20, the tooth extraction process may begin. During the tooth extraction process, the user of the apparatus 10 endeavors to keep the decorative element 60 within the line of sight of the patient so that the visual stimulus provided by the decorative element 60 eases the anxiety felt by the patient. While doing so, the user lightly grips the first and second arms 40, 42 of the handle portion 20 such that the first and second arms 40, 42 are biased into the first position. The user then maneuvers the first and second engagement tips 48, 50 of the first and second arms 40, 42 into the patient's mouth, and further into proximity of the loose tooth. Once the first and second engagement tips 48, 50 of the first and second arms 40, 42 are positioned adjacent to opposite sides of the loose tooth, the user applies pressure to the first and second arms 40, 42 such that the first and second arms 40, 42 move from the first position toward the second position. As the first and second arms 40, 42 reach the second position, the first and second engagement tips 48, 50 of the first and second arms 40, 42 engage the tooth. If the first and second engagement tips 48, 50 are formed of a resilient material, such as rubber, any sounds or sensations that would otherwise be experienced by the patient are thereby dampened. To extract the tooth, the user firmly grips the tooth with the first and second engagement tips 48, 50 of the first and second arms 40, 42 and manipulates the handle portion 20 and the first and second arms 40, 42 to pull the tooth away from the patient's jaw, thereby removing it from the patient's mouth.

While the invention has been described in connection with what is presently considered to be the most practical and preferred embodiment, it is to be understood that the invention is not to be limited to the disclosed embodiments, but to the contrary, it is intended to cover various modifications or equivalent arrangements included within the spirit and scope of the appended claims. The scope is to be accorded the broadest interpretation so as to encompass all such modifications and equivalent structures as is permitted under the law.

What is claimed is:

1. An apparatus for pulling a loose tooth, comprising:
   a first arm having a tool end and a decorative end;
   a second arm having a tool end and a decorative end;
   said first arm and said second arm operatively connected to one another at said decorative ends;
   first and second engagement tips connected to said tool ends of said first and second arms, respectively;
   said tool end of said first arm and said tool end of said second arm moveable between a first position, wherein said tool ends of said first and second arms are adapted to disengage said tooth, and a second position, wherein said tool ends of said first and second arms are adapted to engage said tooth; and
   a decorative element having an attachment member that is releasably received by a receptacle in said decorative ends of said first and second arms for releasably attaching said decorative element to said first and second arms;
   said receptacle having an aperture formed in said decorative ends of said first and second arms; and said attachment member having a post receivable in said aperture to thereby form a friction fit;
   said receptacle extending through said decorative ends between a top surface of said decorative ends and a bottom surface of said decorative ends; and said attachment member receivable in said receptacle adjacent to either of said top surface or said bottom surface of said decorative ends of said first and second arms.

2. The apparatus for pulling loose teeth of claim 1, further comprising:
   said first and second engagement tips formed from a resilient material.

3. The apparatus for pulling loose teeth of claim 1, further comprising:
   said first and second engagement tips fabricated from rubber caps.

4. The apparatus stated in claim 1, further comprising:
   said decorative ends of said first and said second arms integral with one another.

5. The apparatus stated in claim 1, each of said first and second arms further comprising:
   an elongated body; and
   an upturned portion forming an obtuse angle with respect to said elongated body.

6. The apparatus stated in claim 5, each of said first and second arms further comprising:
   a widened portion on said elongated body of said first and second arms.

7. An apparatus for pulling a loose tooth, comprising:
   first and second arms having a tool end and a decorative end, said decorative ends of said first and second arms connected to one another at said decorative ends, and each of said first and second arms having an elongated body;
   said decorative ends of said first and second arms having an aperture extending therethrough, between a top surface of said decorative ends and a bottom surface of said decorative ends;
   first and second widened portions on said elongated bodies of said first and second arms, respectively, for gripping said first and second arms;
   first and second upturned portions forming an obtuse angle with respect to said elongated bodies of said first and second arms;
   first and second engagement tips connected to said upturned portions of said first and second arms, respectively;
   said tool end of said first arm and said tool end of said second arm moveable between a first position, wherein said tool ends of said first and second arms are adapted to disengage said tooth, and a second position, wherein said tool ends of said first and second arms are adapted to engage said tooth; and
   a decorative element having an attachment member that is releasably received by said aperture in said decorative ends of said first and second arms for releasably attaching said decorative element to said first and second arms;
   said attachment member receivable in said aperture such that said decorative element is selectively positionable adjacent to either said top surface or said bottom surface of said decorative ends of said first and second arms.

8. The apparatus stated in claim 7, further comprising:
   said attachment member having a post that cooperates with said aperture to define a friction fit.

9. The apparatus stated in claim 8, further comprising:
   said decorative ends of said first and second arms integral with one another.

10. The apparatus stated in claim 9, further comprising:
    said first and second engagement tips fabricated from rubber caps.

11. The apparatus stated in claim 10, further comprising:
    said first and second arms biased toward said first position.

* * * * *